United States Patent
Ito et al.

(10) Patent No.: US 10,512,833 B2
(45) Date of Patent: Dec. 24, 2019

(54) PRESENTATION METHOD, SWING ANALYSIS APPARATUS, SWING ANALYSIS SYSTEM, SWING ANALYSIS PROGRAM, AND RECORDING MEDIUM

(71) Applicant: SEIKO EPSON CORPORATION, Tokyo (JP)

(72) Inventors: Tsuyoshi Ito, Suwa (JP); Masafumi Sato, Hara-mura (JP); Kenya Hayashi, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 231 days.

(21) Appl. No.: 15/404,998

(22) Filed: Jan. 12, 2017

(65) Prior Publication Data
US 2017/0203187 A1    Jul. 20, 2017

(30) Foreign Application Priority Data
Jan. 15, 2016    (JP) .................... 2016-005848

(51) Int. Cl.
| A63B 71/06 | (2006.01) |
| G06F 16/22 | (2019.01) |
| A63B 69/36 | (2006.01) |
| A63B 102/02 | (2015.01) |
| A63B 102/04 | (2015.01) |
| A63B 102/16 | (2015.01) |
| A63B 102/18 | (2015.01) |

(52) U.S. Cl.
CPC ...... *A63B 71/0619* (2013.01); *A63B 69/3632* (2013.01); *G06F 16/2272* (2019.01); *A63B 2071/0663* (2013.01); *A63B 2071/0666* (2013.01); *A63B 2102/02* (2015.10); *A63B 2102/04* (2015.10); *A63B 2102/16* (2015.10); *A63B 2102/18* (2015.10); *A63B 2102/182* (2015.10); *A63B 2220/34* (2013.01); *A63B 2220/40* (2013.01); *A63B 2220/51* (2013.01); *A63B 2225/50* (2013.01)

(58) Field of Classification Search
CPC ............ A63B 71/0619; A63B 71/1122; A63B 71/1124; A63B 69/3632; A63B 2102/02; A63B 2102/04; A63B 2102/16; A63B 2102/18; A63B 2102/182; A63B 2071/0663; A63B 2071/0666; A63B 2220/34; A63B 2220/49; A63B 2220/50; A63B 2220/51; G06F 16/2272; A61B 5/1122; A61B 5/1124
USPC ........................................ 473/221
See application file for complete search history.

(56) References Cited

U.S. PATENT DOCUMENTS

| 2004/0003402 A1* | 1/2004 | McKenna, Jr. ........ G06F 3/0481 725/46 |
| 2006/0166737 A1* | 7/2006 | Bentley ................ A61B 5/1122 463/30 |
| 2016/0310820 A1* | 10/2016 | Kline ................. A63B 71/0619 |

FOREIGN PATENT DOCUMENTS

JP    2015-180276 A    10/2015

* cited by examiner

*Primary Examiner* — Omkar A Deodhar
*Assistant Examiner* — Wei Lee
(74) *Attorney, Agent, or Firm* — Oliff PLC

(57) ABSTRACT

A presentation method includes performing analysis on a swing by using output data from an inertial sensor measuring the swing of an exercise appliance, finishing the analysis, and presenting analysis information based on at least one preset index regarding the swing, on the basis of finishing of the analysis.

22 Claims, 8 Drawing Sheets

PRESENTATION METHOD, SWING ANALYSIS APPARATUS, SWING ANALYSIS SYSTEM, SWING ANALYSIS PROGRAM, AND RECORDING MEDIUM

BACKGROUND

1. Technical Field

The present invention relates to a presentation method, a swing analysis apparatus, a swing analysis system, a swing analysis program, and a recording medium.

2. Related Art

There is a technique in which a swing trajectory of a golf club, a racket, or a bat as an exercise appliance in sports such as golf, tennis, or baseball is analyzed, and an athletic ability of a player is enhanced by improving a swing trajectory. As an example of such a technique, for example, JP-A-2015-180276 discloses a golf support device. The golf support device disclosed in JP-A-2015-180276 measures items related to a swing of a golf club, such as a head speed or a ball speed, and analyzes the swing of the golf club. Analysis results are displayed on a display section provided in the golf support device.

However, in the technique disclosed in JP-A-2015-180276, since swing analysis results cannot be displayed on the display section unless a user operates the golf support device so as to give an instruction, the user has to sequentially operate the golf support device in a case where swings are continuously performed with the golf club in order to perform analysis, and thus there is a problem of inconvenience that efficient practice cannot be performed.

SUMMARY

An advantage of some aspects of the invention is to solve at least a part of the problems described above, and the invention can be implemented as the following aspects or application examples.

Application Example 1

A presentation method according to this application example includes performing analysis on a swing by using output data from an inertial sensor measuring the swing of an exercise appliance; finishing the analysis; and presenting at least one preset index of analysis information regarding the swing, on the basis of finishing of the analysis.

According to the presentation method of the application example, at least one index of analysis information of a measured swing is presented on the basis of finishing of analysis of a swing of an exercise appliance using an inertial sensor. In the above-described way, analysis information regarding the swing is presented for each swing finishing timing even without an instruction or the like from a user. Consequently, a user can obtain swing analysis information for each swing finishing timing even if the user continuously performs swings with an exercise appliance. Therefore, it is possible to improve convenience in that the user can perform practice while continuously performing swings with an exercise appliance. Consequently, a user can perform highly efficient practice.

Application Example 2

In the presentation method of the application example, it is preferable that, in the presenting of the index, at least two preset indexes are sequentially presented, and the indexes are switched according to a preset switching timing.

According to this application example, since at least two preset indexes (presentation content items) are automatically switched according to a preset switching timing, it is possible to sequentially obtain swing analysis information even without an instruction or the like from a user. In the above-described way, it is possible to obtain a plurality of pieces of swing analysis information without troubling a user, and thus to further improve convenience.

Application Example 3

It is preferable that the presentation method of the application example further includes setting the index before performing the analysis.

According to this application example, since an index desired to be presented can be selected and set among pieces of swing analysis information, it is possible to efficiently present swing analysis information desired to be obtained by a user, and thus to further improve convenience.

Application Example 4

In the presentation method of the application example, it is preferable that, in the presenting of the index, the index is preferentially presented on the basis of a plurality of pieces of swing analysis information.

According to this application example, a set index is preferentially presented on the basis of a plurality of pieces of swing analysis information, and thus it is possible to easily understand a tendency of repeatedly performed swings.

Application Example 5

In the presentation method of the application example, it is preferable that, in the presenting of the index, the index is presented along with information corresponding to the index among pieces of analysis information regarding a swing which is different from the swing.

According to this application example, since a presented index of analysis information regarding a swing is displayed along with an index of analysis information regarding a different swing, corresponding to the index of the analysis information regarding the swing, it is possible to compare the pieces of analysis information regarding the different swings with each other, so as to objectively determine a difference between the swings or to easily determine the quality of a swing state.

The above-described analysis information regarding a different swing includes, for example, swing analysis data regarding other people, data regarding a swing performed previously, and an average value of data regarding a swing.

Application Example 6

In the presentation method of the application example, it is preferable that, in the presenting of the index, the index is presented as image information.

According to this application example, an analysis result can be visually recognized as image information. Consequently, a swing state can be recognized or determined in detail and objectively.

Application Example 7

In the presentation method of the application example, it is preferable that, in the presenting of the index, the index is presented as voice information.

According to this application example, an analysis result can be obtained as voice information while performing a swing, and thus it is possible to perform more efficient practice.

Application Example 8

In the presentation method of the application example, it is preferable that, in the presenting of the index, comment is presented along with the index.

According to this application example, since comment is presented along with analysis information related to a set index, a user can be promoted to understand an analysis result or can appropriately cope with the analysis result.

Application Example 9

In the presentation method of the application example, it is preferable that the comment is advice information.

According to this application example, since advice information is presented along with analysis information related to a set index, it is possible to accurately cope with improvement of a swing.

Application Example 10

In the presentation method of the application example, it is preferable that, in the presenting of the index, a swing trajectory based on the analysis information is presented along with the index.

According to this application example, since a swing trajectory based on analysis information is presented along with the analysis information related to a set index, it is possible to objectively and easily visually recognize a series of swing actions as image information. Consequently, it is possible to more easily determine the quality of a swing state.

Application Example 11

A swing analysis apparatus according to this application example includes an analysis section that performs analysis on a swing by using output data from an inertial sensor measuring the swing of an exercise appliance, so as to generate pieces of analysis information; and a processing section that forms presentation data on the basis of the pieces of analysis information so as to output the presentation data, in which the processing section presents at least one preset index of the analysis information, on the basis of finishing of the analysis.

According to the swing analysis apparatus of the application example, the processing section presents at least one index of swing analysis information, generated by the analysis section, on the basis of finishing of analysis of a swing of an exercise appliance using an inertial sensor. In the above-described way, analysis information regarding the swing is presented even without an instruction or the like from a user. Consequently, a user can obtain swing analysis information for each swing finishing timing even if the user continuously performs swings with an exercise appliance. Therefore, it is possible to provide a swing analysis apparatus capable of improving convenience in that a user can perform practice while continuously performing swings with an exercise appliance. Therefore, a user can perform highly efficient practice.

Application Example 12

In the swing analysis apparatus of the application example, it is preferable that the processing section presents at least two preset indexes, and switches the indexes according to a preset switching timing.

According to this application example, the processing section automatically switches at least two presentation content items according to a preset switching timing. Consequently, a user can sequentially obtain at least two pieces of swing analysis information without giving an instruction. In the above-described way, it is possible to obtain a plurality of pieces of swing analysis information without troubling a user, and thus to further improve convenience.

Application Example 13

It is preferable that the swing analysis apparatus of the application example further includes an input section that is used to input the selected index before the swing is analyzed.

According to this application example, since an index desired to be presented can be selected among pieces of swing analysis information and can be input to the input section before a swing is started, it is possible to efficiently present swing analysis information desired to be obtained by a user, and thus to further improve convenience.

Application Example 14

In the swing analysis apparatus of the application example, it is preferable that the processing section preferentially presents the index on the basis of a plurality of pieces of swing analysis information.

According to this application example, a set index is preferentially presented on the basis of a plurality of pieces of swing analysis information, and thus a user can easily understand a tendency of a plurality of swings which are repeatedly performed.

Application Example 15

In the swing analysis apparatus of the application example, it is preferable that the processing section presents the index along with information corresponding to the index among pieces of analysis information regarding a swing which is different from the swing.

According to this application example, since a presented index of analysis information regarding a swing is displayed along with an index of analysis information regarding a different swing, corresponding to the index of the analysis information regarding the swing, it is possible to compare the pieces of analysis information regarding the different swings with each other, so as to objectively determine a difference between the swings or to easily determine the quality of a swing state.

The above-described analysis information regarding a different swing includes, for example, swing analysis data regarding other people, data regarding a swing performed previously, and an average value of data regarding a swing.

Application Example 16

In the swing analysis apparatus of the application example, it is preferable that the processing section includes an image data generation section that generates image data on the basis of the analysis information, and the swing analysis apparatus further includes a display section that presents the index as image information based on the image data.

According to this application example, an analysis result can be visually recognized as image information, and thus a swing state can be recognized or determined in detail and objectively.

Application Example 17

In the swing analysis apparatus of the application example, it is preferable that the processing section includes a voice data generation section that generates voice data on the basis of the analysis information, and the swing analysis apparatus further includes a sound output section that presents the index as voice information based on the voice data.

According to this application example, an analysis result can be obtained as voice information while performing a swing, and thus it is possible to perform more efficient practice.

Application Example 18

In the swing analysis apparatus of the application example, it is preferable that the processing section presents comment along with the index.

According to this application example, since comment is presented along with analysis information related to a set index, a user can be promoted to understand an analysis result or can appropriately cope with the analysis result.

Application Example 19

In the swing analysis apparatus of the application example, it is preferable that the comment is advice information.

According to this application example, since advice information is presented along with analysis information related to a set index, it is possible to accurately cope with improvement of a swing.

Application Example 20

In the swing analysis apparatus of the application example, it is preferable that the processing section displays a swing trajectory based on the analysis information on the display section along with the index.

According to this application example, since a swing trajectory based on analysis information is presented along with the analysis information related to a set index, it is possible to objectively and easily visually recognize a series of swing actions as image information. Consequently, it is possible to more easily determine the quality of a swing state.

Application Example 21

A swing analysis system according to this application example includes any one of the swing analysis apparatuses; and an inertial sensor.

According to the swing analysis system of the application example, at least one index of swing analysis information based on measured data which is obtained by an inertial sensor is presented on the basis of a determination of finishing of measurement of a swing of an exercise appliance using a swing analysis apparatus. In the above-described way, analysis information regarding the swing is presented even without an instruction or the like from a user. Consequently, a user can obtain swing analysis information for each swing finishing timing even if the user continuously performs swings with an exercise appliance. Therefore, it is possible to provide a swing analysis system capable of improving convenience in that a user can perform practice while continuously performing swings with an exercise appliance. Therefore, a user can perform highly efficient practice by using the present swing analysis system.

Application Example 22

A swing analysis program according to this application example causes a computer to execute performing analysis on a swing by using output data from an inertial sensor measuring the swing of an exercise appliance; finishing the analysis; and presenting at least one preset index of analysis information regarding the analyzed swing, on the basis of finishing of the analysis.

According to the swing analysis program of the application example, the program causes a computer to execute presenting at least one index of swing analysis information based on measured data which is obtained by an inertial sensor on the basis of a determination of finishing of measurement of a swing of an exercise appliance using a swing analysis apparatus. In the above-described way, analysis information regarding the swing is presented even without an instruction or the like from a user. Consequently, a user can obtain swing analysis information for each swing finishing timing even if the user continuously performs swings with an exercise appliance. Therefore, it is possible to improve convenience in that a user can perform practice while continuously performing swings with an exercise appliance.

Application Example 23

A recording medium according to this application example stores a program causing a computer to execute performing analysis on a swing by using output data from an inertial sensor measuring the swing of an exercise appliance; finishing the analysis; and presenting at least one preset index of analysis information regarding the analyzed swing, on the basis of finishing of the analysis.

According to the recording medium of the application example, by executing a computer on the basis of the stored program, at least one index of swing analysis information based on measured data which is obtained by an inertial sensor is presented on the basis of a determination of finishing of measurement of a swing of an exercise appliance using a swing analysis apparatus. In the above-described way, analysis information regarding the swing is presented even without an instruction or the like from a user. Consequently, a user can obtain swing analysis information for each swing finishing timing even if the user continuously performs swings with an exercise appliance. Therefore, it is possible to improve convenience in that a user can perform practice while continuously performing swings with an exercise appliance.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described with reference to the drawings. The embodiments described below are not intended to improperly limit the content of the invention disclosed in the appended claims. In addition, all constituent elements described below are not essential constituent elements of the invention.

Figure 1:
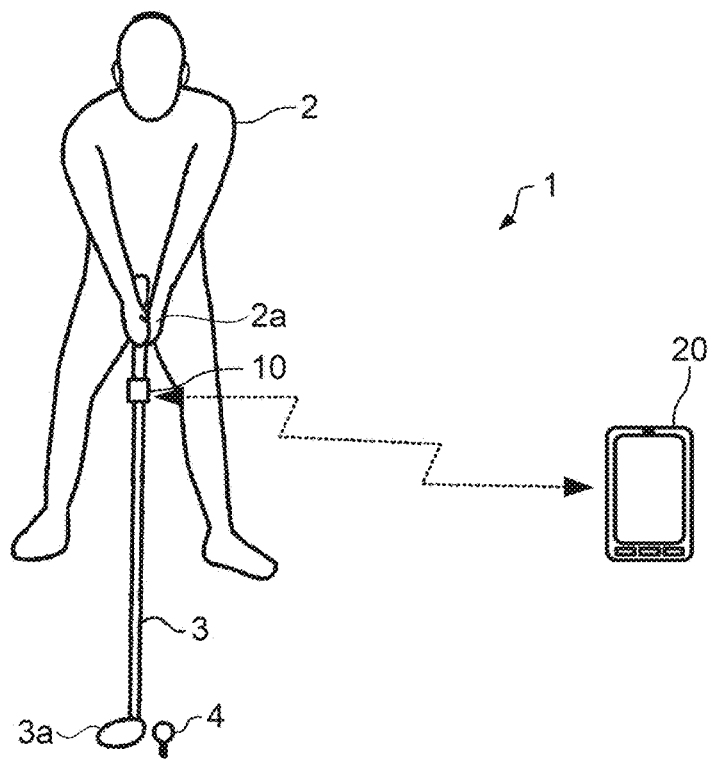
FIG. 1 is a diagram illustrating a summary of a swing analysis system.
Figure 2:
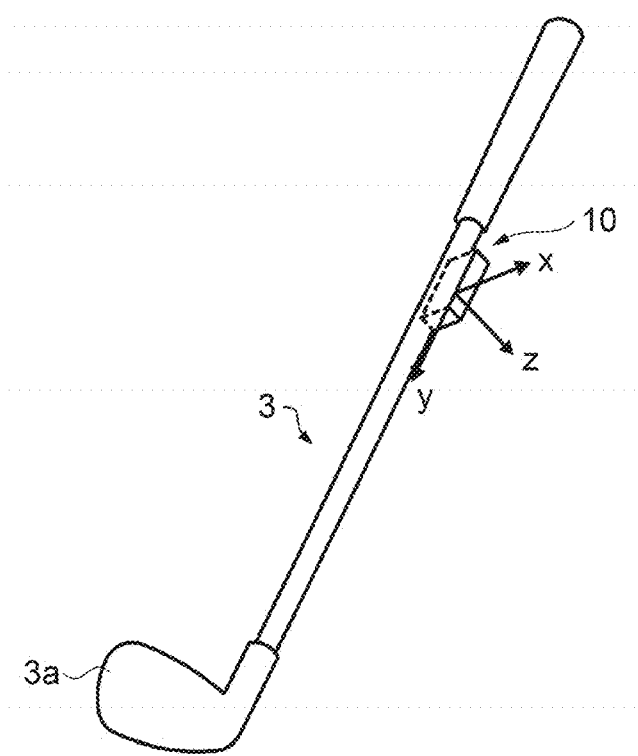
FIG. 2 is a diagram illustrating examples of a position at which and a direction in which the sensor unit is attached.
Figure 3:
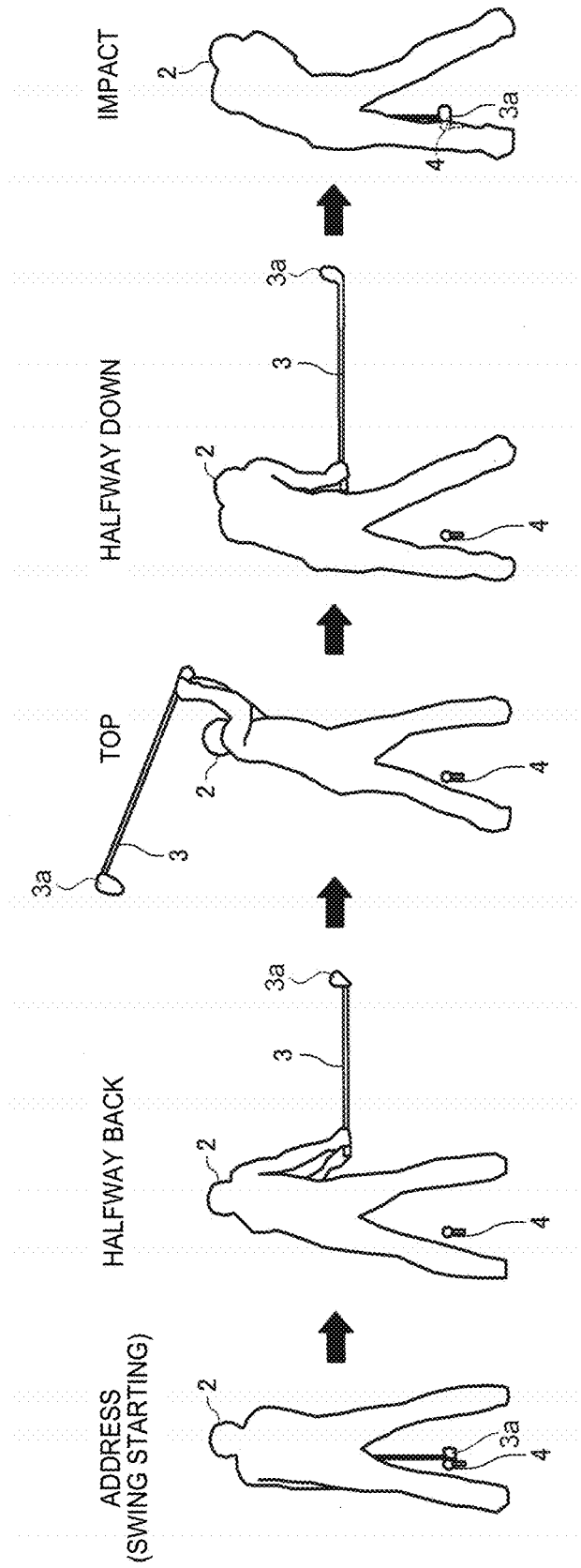
FIG. 3 is a diagram illustrating swing actions.
Figure 4:
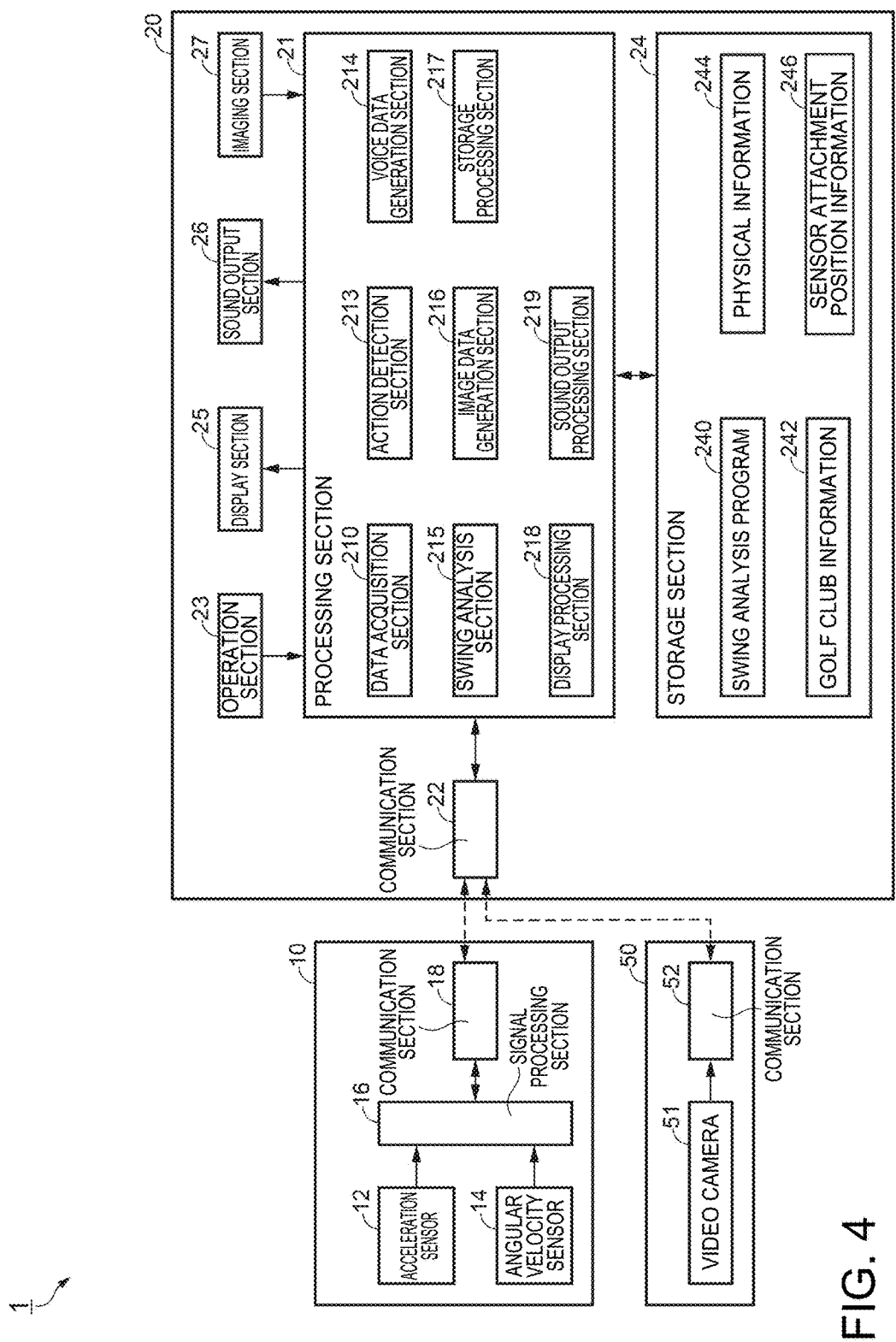
FIG. 4 is a diagram illustrating a configuration example of the swing analysis system.

Swing Analysis (Motion Analysis) System 1-1. Summary of Swing Analysis (Motion Analysis) System FIG. 1 is a diagram illustrating a summary of a swing analysis system of the present embodiment. FIG. 2 is a diagram illustrating examples of a position at which and a direction in which the sensor unit is attached. FIG. 3 is a diagram illustrating a series of swing actions. FIG. 4 is a diagram illustrating a configuration example of the swing analysis system.

As illustrated in FIG. 1, a swing analysis system 1 of the present embodiment is configured to include a sensor unit 10 (an example of an inertial sensor), and a motion analysis display apparatus 20 as a swing analysis apparatus. The swing analysis system 1 may be configured to include a recorder 50 as illustrated in FIG. 4. The swing analysis system 1 analyzes a swing (hereinafter, referred to as a golf swing) of a golf club 3 performed by a user (subject) 2 in order to hit a golf ball 4 as a target. In the present embodiment, a swing analysis apparatus analyzing a golf swing will be exemplified, but a swing analysis apparatus according to the invention is applicable to swing analysis of various exercise appliances used to perform swings, such as rackets in tennis, badminton, and table tennis, and bats in baseball or softball.

The sensor unit 10 as a measurement unit can measure acceleration generated in each axial direction of three axes and angular velocity generated around each of the three axes by using provided inertial sensors (an acceleration sensor 12 and an angular velocity sensor 14 illustrated in FIG. 4), and is attached to a golf club 3 (an example of an exercise appliance) in the present embodiment.

In the present embodiment, as illustrated in FIG. 2, the sensor unit 10 as a measurement unit is attached to a part of a shaft of the golf club 3 so that one axis of three detection axes (an x axis, a y axis, and a z axis), for example, the y axis matches a longitudinal direction of the shaft. Preferably, the sensor unit 10 is attached to a position close to a grip to which impact during ball hitting is hardly forwarded and a centrifugal force is not applied during a swing. The shaft is a shaft portion other than a head 3a of the golf club 3 and also includes the grip. However, the sensor unit 10 may be attached to a part (for example, the hand or a glove) of the user 2 as a subject, and may be attached to an accessory such as a wristwatch.

In the present embodiment, swing analysis (motion analysis) is described by exemplifying a swing of the golf club 3. In a golf swing, for example, a series of swing actions as illustrated in FIG. 3 is performed. Specifically, as illustrated in FIG. 3, the swing actions include actions starting from an address position in a standing still state, and reaching impact at which the golf ball 4 is hit through respective states of halfway back at which the shaft of the golf club 3 becomes horizontal during a backswing after starting a swing (backswing), a top at which the swing changes from the backswing to a downswing, and halfway down at which the shaft of the golf club 3 becomes horizontal during the downswing. After the impact, the series of swing actions is completed through follow-through (not illustrated).

1-2. Configuration of Swing Analysis (Motion Analysis) System

FIG. 4 is a diagram illustrating a configuration example (configuration examples of the sensor unit 10, the motion analysis display apparatus 20 as a swing analysis apparatus, and the recorder 50) of the swing analysis (motion analysis) system 1 of the present embodiment. As illustrated in FIG. 4, in the present embodiment, the sensor unit 10 is configured to include an acceleration sensor 12 and an angular velocity sensor 14 as inertial sensors, a signal processing section 16, and a communication section 18.

The acceleration sensor 12 as an inertial sensor measures respective accelerations in three axial directions which intersect (ideally, orthogonal to) each other, and outputs digital signals (acceleration data) corresponding to magnitudes and directions of the measured three-axis accelerations.

The angular velocity sensor 14 as an inertial sensor measures respective angular velocities in three axial directions which intersect (ideally, orthogonal to) each other, and outputs digital signals (angular velocity data) corresponding to magnitudes and directions of the measured three-axis angular velocities.

The signal processing section 16 receives the acceleration data and the angular velocity data (measured data) from the acceleration sensor 12 and the angular velocity sensor 14, respectively, adds time information thereto, stores the data in a storage portion (not illustrated), adds time information to the stored measured data (an example of attitude or position information) so as to generate packet data conforming to a communication format, and outputs the packet data to the communication section 18.

Ideally, the acceleration sensor 12 and the angular velocity sensor 14 are provided in the sensor unit 10 so that the three axes thereof match three axes (an x axis, a y axis, and a z axis) of an orthogonal coordinate system (sensor coordinate system) defined for the sensor unit 10, but, actually, errors occur in installation angles. Therefore, the signal processing section 16 performs a process of converting the acceleration data and the angular velocity data into data in the xyz coordinate system by using a correction parameter which is calculated in advance according to the installation angle errors.

The signal processing section 16 may perform a process of correcting the temperatures of the acceleration sensor 12 and the angular velocity sensor 14. Alternatively, the acceleration sensor 12 and the angular velocity sensor 14 may have a temperature correction function.

The acceleration sensor 12 and the angular velocity sensor 14 may output analog signals, and, in this case, the signal processing section 16 may A/D convert an output signal from the acceleration sensor 12 and an output signal from the angular velocity sensor 14 so as to generate measured data (acceleration data and angular velocity data), and may generate communication packet data by using the data.

The communication section 18 performs a process of transmitting packet data received from the signal processing section 16 to the motion analysis display apparatus 20, or a process of receiving a control command from the motion analysis display apparatus 20 and sending the control command to the signal processing section 16. The signal processing section 16 performs various processes corresponding to control commands.

The motion analysis display apparatus 20 as a swing analysis apparatus is implemented by, for example, an information terminal (client terminal) such as a smart phone, a personal computer, a head mounted display (HMD) 500 which will be described later, or an arm mounted analysis display apparatus 600 which will be described later. The motion analysis display apparatus 20 is configured to include a processing section 21 (an example of a processing section), a communication section 22, an operation section 23, a storage section 24, a display section 25, a sound output section 26, and an imaging section 27.

The communication section 22 performs a process of receiving packet data transmitted from the sensor unit 10 and sending the packet data to the processing section 21, or a process of transmitting a control command from the processing section 21 to the sensor unit 10.

The operation section 23 as an input section performs a process of acquiring operation data from the user (subject) 2 and sending the operation data to the processing section 21. The operation section 23 may be, for example, a touch panel type display, a button, a key, or a microphone. In other words, the operation section 23 functions as an input section which allows operation data or the like to be input. The user (subject) 2 may input desired operation data via the operation section 23. Data acquired from the operation section 23 may include, for example, a swing time (date and time), user identification information (user ID), the sex of the user 2, golf club information 242, physical information 244 of the user 2, and sensor attachment position information 246 corresponding to position information of the sensor unit 10.

Data acquired from the operation section 23 may include indexes related to input analysis information, the analysis information being selected as information which is presented (through image display or voice notification) after analysis is finished. Consequently, since analysis information to be presented (through image display or voice notification) is selected from among swing analysis information pieces, and is set in advance, it is possible to improve convenience in that desired presentation (through image display or voice notification) can be automatically performed without troubling the user 2 when a swing is completed.

The storage section 24 is constituted of, for example, various IC memories such as a read only memory (ROM), a flash ROM, and a random access memory (RAM), or a recording medium such as a hard disk or a memory card.

The storage section 24 stores a program for the processing section 21 performing various calculation processes or a control process, or various programs or data for realizing application functions. Particularly, in the present embodiment, the storage section 24 stores a swing analysis program (motion analysis program) 240 which is read by the processing section 21 and executes a swing analysis process. The swing analysis program 240 may be stored in a non-volatile recording medium (an example of a recording medium) in advance, or the swing analysis program 240 may be received from a server by the processing section 21 via a network, and may be stored in the storage section 24.

The storage section 24 stores the golf club information 242, the physical information 244, and the sensor attachment position information 246 which is position information of the sensor unit 10, as information used for a swing analysis process.

The golf club information 242 is information indicating a specification of the golf club 3 used by the user 2. For example, the user 2 may operate the operation section 23 so as to input golf club information regarding the golf club 3 in use, and the input golf club information may be used as the golf club information 242. Alternatively, in step S90 in FIG. 5 which will be described later, the user 2 may sequentially input type numbers of the golf club 3 (alternatively, selects a type number from a type number list) so that specification information (for example, information regarding a length of the shaft, a position of the centroid thereof, a lie angle, a face angle, a loft angle, and the like) for each type number is stored in the storage section 24 in advance. In this case, specification information of an input type number may be used as the golf club information 242.

The physical information 244 is information indicating a physique (a height of the waist, a height of the neck, a length of the arm, and the like) of the user 2. For example, the user 2 may input physical information by operating the operation section 23, and the input physical information may be used as the physical information 244.

The sensor attachment position information 246 is information indicating an attachment position of the sensor unit 10 in the golf club 3. For example, in step S90 in FIG. 5, the user 2 may input an attachment position of the sensor unit 10 and a distance to the grip of the golf club 3 by operating the operation section 23, and the input distance information may be used as the sensor attachment position information 246. Alternatively, the sensor unit 10 may be attached at a defined predetermined position (for example, a distance of 20 cm from the grip), and thus information regarding the predetermined position may be stored as the sensor attachment position information 246 in advance.

The storage section 24 is used as a work area of the processing section 21, and temporarily stores data which is input from the operation section 23, results of calculation executed by the processing section 21 according to various programs, and the like. The storage section 24 may store data which is required to be preserved for a long period of time among data items generated through processing of the processing section 21.

The display section 25 displays a processing result in the processing section 21 as text, a graph, a table, animation, and other images. The display section 25 may be, for example, a CRT, an LCD, a touch panel type display, and a head mounted display (HMD). A single touch panel type display may realize functions of the operation section 23 and the display section 25.

The sound output section 26 outputs a processing result (analysis information) in the processing section 21 so as to present the processing result as a sound such as a voice or a buzzer sound. The sound output section 26 may be, for example, a speaker or a buzzer.

The imaging section 27 includes a light reception unit (not illustrated) provided with an optical lens (imaging optical system) or a charge coupled device (CCD) (not illustrated). The imaging section 27 may capture an image of a subject (user 2) and store imaging data in the storage section 24, or may send imaging data to an image data generation section 216, and display image data generated by the image data generation section 216 on the display section 25.

The processing section 21 performs a process of transmitting a control command to the sensor unit 10, various computation processes on data which is received from the sensor unit 10 via the communication section 22, and other various control processes, according to various programs. By executing the swing analysis program (motion analysis program) 240, the processing section 21 functions as a data acquisition section 210, an action detection section 213 as a detection section, a voice data generation section 214, a swing analysis section 215 as an analysis section, the image data generation section 216, a storage processing section 217, a display processing section 218, and a sound output processing section 219.

The data acquisition section 210 performs a process of receiving packet data which is received from the sensor unit 10 by the communication section 22, acquiring time information and measured data in the sensor unit 10 from the received packet data, and sending the time information and the measured data to the storage processing section 217.

The action detection section 213 as a detection section performs a process of detecting at least one of swing actions of the user 2 on the basis of the measured data acquired by the data acquisition section 210. The action detection section 213 detects (specifies) a swing starting timing, a top timing, an impact timing, and a swing finishing timing on the basis of a combined value of angular velocities (a norm of angular velocity) or the like.

As an example of a method of detecting (specifying) each timing, a timing (time point) at which a norm of angular velocity is the minimum in an interval of a top in a swing specified before an impact timing may be detected (specified) as a top timing in the swing. For example, a timing at which a norm of angular velocity is the minimum in an address interval specified before a top may be detected (specified) as a swing starting timing. It is hardly considered that, in a typical swing action, a swing action is stopped from a standing still state (address) to a top, and thus a timing at which a norm of angular velocity is the minimum in an address interval specified before the top may be captured as a swing starting timing. For example, a timing at which a norm of angular velocity is the minimum after impact may be detected as a swing finishing timing.

The swing analysis section 215 as an analysis section performs a process of analyzing a swing of the user 2 by using the measured data output from the sensor unit 10. Specifically, the swing analysis section 215 computes an offset amount included in the measured data by using the measured data (acceleration data and angular velocity data) for the user 2 during standing still (at address), stored in the storage section 24. Next, the swing analysis section 215 subtracts the offset amount from measured data after starting the swing, stored in the storage section 24, so as to perform bias correction, and computes a position and an attitude of the sensor unit 10 during a swing action of the user 2 (during an action in step S106 in FIG. 5) by using the bias-corrected measured data.

For example, the swing analysis section 215 computes a position (initial position) of the sensor unit 10 during standing still (at address) of the user 2 in an XYZ coordinate system (global coordinate system) by using acceleration data measured by the acceleration sensor 12, the golf club information 242, and the sensor attachment position information 246, and integrates subsequent acceleration data so as to compute coordinates of a position from the initial position of the sensor unit 10 in a time series. Since the user 2 performs the action in step S103 in FIG. 5, an X coordinate of the initial position of the sensor unit 10 is 0. As illustrated in FIG. 2, since the y axis of the sensor unit 10 matches the longitudinal direction of the shaft of the golf club 3, and the acceleration sensor 12 measures only the gravitational acceleration during standing still of the user 2, the swing analysis section 215 can compute an inclined angle of the shaft by using y axis acceleration data. The swing analysis section 215 obtains a distance $L_{SH}$ (not illustrated) between the sensor unit 10 and the head 3a on the basis of the golf club information 242 (a length of the shaft), and the sensor attachment position information 246 (a distance from the grip), and sets, as the initial position (attitude information during standing still) of the sensor unit 10, a position of the sensor unit 10 at the distance $L_{SH}$ from the origin in a negative direction of the y axis of the sensor unit 10, specified by the inclined angle of the shaft when a position of the head 3a is used as the origin (0,0,0).

The swing analysis section 215 computes an attitude (initial attitude) of the sensor unit 10 during standing still (at address) of the user 2 in the XYZ coordinate system (global coordinate system) by using acceleration data measured by the acceleration sensor 12, and computes changes in attitudes from the initial attitude of the sensor unit 10 by performing rotation calculation using angular velocity data which is subsequently measured by the angular velocity sensor 14. An attitude of the sensor unit 10 may be expressed by, for example, rotation angles (a roll angle, a pitch angle, and a yaw angle) about the x axis, the y axis, and the z axis, or a quaternion. Since the acceleration sensor 12 measures only the gravitational acceleration during standing still of the user 2, the swing analysis section 215 can specify angles respectively formed between the x axis, the y axis, and the z axis of the sensor unit 10, and the gravitational direction, by using three-axis acceleration data. Since the user 2 performs the action in step S103 in FIG. 5, the y axis of the sensor unit 10 is present on a YZ plane during standing still of the user 2, and thus the swing analysis section 215 can specify the initial attitude of the sensor unit 10.

The swing analysis section 215 may detect specific timings (for example, timings of swing starting, halfway back, a top, halfway down, and impact) during a swing action of the user 2. For example, the swing analysis section 215 computes a combined value of measured data (acceleration data or angular velocity data) output from the sensor unit 10, and specifies timings (time points) of swing starting and a top on the basis of the combined value.

On the basis of a position of the sensor unit 10 at each time point (timing), an attitude of the sensor unit 10 at the time point, the golf club information 242, and the sensor attachment position information 246, the swing analysis section 215 computes a position of the head 3a at the time point. On the basis of a position of the sensor unit 10 at each time point of a swing, an attitude of the sensor unit 10 at the time point, the golf club information 242, and the sensor attachment position information 246, the swing analysis section 215 computes a position of the grip at the time point. The swing analysis section 215 generates swing trajectory data on the basis of obtained data regarding a series of swing actions.

The signal processing section 16 of the sensor unit 10 may compute an offset amount of measured data so as to perform bias correction on the measured data, and the acceleration sensor 12 and the angular velocity sensor 14 may have a bias correction function. In this case, it is not necessary for the swing analysis section 215 to perform bias correction on the measured data.

The image data generation section 216 performs a process of generating image data for displaying determination result information (analysis information) on the display section 25. The image data generation section 216 performs a process of generating image data for displaying imaging data captured by the imaging section 27 or the recorder 50 on the display section 25 as an image.

The storage processing section 217 performs a process of receiving time information and measured data from the data acquisition section 210 and storing the time information and the measured data in the storage section 24 in correlation with each other. The storage processing section 217 performs a process of storing imaging data captured by the imaging section 27 or the recorder 50 in the storage section 24.

The storage processing section 217 performs read/write processes of various programs or various data for the storage section 24. The storage processing section 217 performs not only the process of storing the time information and the measured data received from the data acquisition section 210 in the storage section 24 in correlation with each other, but also a process of storing determination result information or the like generated by the swing analysis section 215, in the storage section 24.

The display processing section 218 performs a process of displaying various images (including text, symbols, and the like in addition to an image corresponding to the image data generated by the image data generation section 216) on the display section 25. For example, the display processing section 218 displays, on the display section 25, an image corresponding to the image data generated by the image data generation section 216, or text or the like indicating a determination result in the swing analysis section 215 automatically or according to an index selected through an input operation performed by the user 2 after a swing action of the user 2 is completed. Alternatively, a display section (not illustrated) may be provided in the sensor unit 10, or another display apparatus (not illustrated) may be provided, and the display processing section 218 may transmit image data to the sensor unit 10 via the communication section 22, so that various images, text, or the like is displayed on the display section of the sensor unit 10 or another display apparatus.

The display processing section 218 displays analysis information corresponding to at least two indexes (that is, a plurality of indexes) selected through an input operation performed by the user 2, on the display section 25 as images. The display content items of at least two images displayed on the display section 25 are automatically switched according to a preset switching timing, and thus the two images are displayed as images having different display content items.

As mentioned above, at least two display (presentation) content items are automatically displayed in a switching manner according to a set switching timing, and thus the user 2 can obtain analysis information regarding a plurality of swings without inconvenience such as indication of the display content.

The display processing section 218 may preferentially display analysis information corresponding to at least two indexes selected through an input operation performed by the user 2 among pieces of analysis information which are generated by using measured data obtained on the basis of a plurality of swings.

Through the display, analysis information based on measurement of a plurality of swings is preferentially displayed, and thus the user 2 can easily understand a tendency of the plurality of swings which are repeatedly performed.

The display processing section 218 may cause the display section 25 to display not only analysis information corresponding to at least two indexes selected through an input operation performed by the user 2 and displayed as images, but also information corresponding to at least two indexes selected among pieces of analysis information regarding a swing which is different from a swing related to the images.

Through the display, a presented index of analysis information regarding a swing is displayed along with an index of analysis information regarding a different swing, corresponding to the analysis information regarding the swing. Therefore, the user 2 can compare the pieces of analysis information regarding the different swings with each other, so as to objectively determine a difference between the swings or to easily determine the quality of a swing state. The above-described analysis information regarding a different swing may include, for example, swing analysis data regarding other people, data regarding a swing performed previously, and an average value of data regarding a swing.

The display processing section 218 may cause the display section 25 to display comment along with analysis information corresponding to at least two indexes selected through an input operation performed by the user 2 and displayed as images. The comment is preferably advice information for an analysis result.

As mentioned above, for example, comment such as advice information is displayed along with an index of analysis information, and thus the user 2 can be promoted to understand an analysis result or can appropriately cope with the analysis result.

The display processing section 218 may display a swing trajectory which is obtained on the basis of an analysis result or the like in the swing analysis section 215 on the display section 25 as image information along with analysis information corresponding to at least two indexes selected through an input operation performed by the user 2 and displayed on the display section 25 as images.

As mentioned above, a swing trajectory is displayed along with an index of analysis information, and thus it is possible to objectively and easily visually recognize a series of swing actions as image information. Consequently, the user 2 can more easily determine the quality or the like of a swing state.

The sound output processing section 219 performs a process of outputting various sounds (including voices based on voice data generated by the voice data generation section 214, buzzer sounds, and the like) from the sound output section 26. For example, the sound output processing section 219 outputs, from the sound output section 26, a voice based on voice data generated by the voice data generation section 214, a buzzer sound, or the like automatically or according to an index selected through an input operation performed by the user 2 after a swing action of the user 2 is completed. When a predetermined input operation is performed, the sound output processing section 219 may read various pieces of information stored in the storage section 24, and may cause the sound output section 26 to output a sound or a voice for swing analysis. Alternatively, the sound output section 26 may be provided in the sensor unit 10, and the sound output processing section 219 may transmit various items of sound data or voice data to the sensor unit 10 via the communication section 22, and may output various sounds or voices from the sound output section of the sensor unit 10.

As mentioned above, analysis information or the like is presented as voice information based on voice data, and thus the user 2 can perform more efficient practice by obtaining an analysis result as voice information while performing a swing.

The sound output processing section 219 causes the sound output section 26 to perform a notification of analysis information corresponding to at least two indexes (that is, a plurality of indexes) selected through an input operation performed by the user 2 as voice information. The content items of at least two pieces of voice information of which the notification is performed by the sound output section 26 are automatically switched according to a preset switching timing, and thus a notification of voice information in which different pieces of analysis information are presented is performed.

As mentioned above, at least two presentation content items are automatically switched according to a set switching timing so that notifications of different pieces of analysis information are performed as voice information, and thus the user 2 can obtain analysis information regarding a plurality of swings without inconvenience such as indication of the display content.

The sound output processing section 219 may preferentially perform a notification, as voice information, of analysis information corresponding to at least two indexes selected through an input operation performed by the user 2 among pieces of analysis information which are generated by using measured data obtained on the basis of a plurality of swings.

Through the notification, analysis information based on measurement of a plurality of swings is preferentially presented, and thus the user 2 can easily understand a tendency of the plurality of swings which are repeatedly performed.

The sound output processing section 219 may cause the sound output section 26 to perform not only a notification of analysis information corresponding to at least two indexes selected through an input operation performed by the user 2 as voice information, but also a notification of analysis information corresponding to at least two indexes selected among pieces of analysis information regarding a swing which is different from a swing related to the voice information.

Through the notification, it is possible to perform not only a notification of a presented index of analysis information regarding a swing but also a notification of an index of analysis information regarding a swing which is different from the swing. Therefore, the user 2 can compare the pieces of analysis information regarding the different swings with each other, so as to objectively determine a difference between the swings or to easily determine the quality of a swing state.

The sound output processing section 219 may cause the sound output section 26 to perform a notification of comment as voice information along with a notification of analysis information corresponding to at least two indexes selected through an input operation performed by the user 2 as voice information. The comment is preferably advice information for an analysis result.

As mentioned above, for example, a notification of comment such as advice information is performed as voice information along with a notification of an index of analysis information, and thus the user 2 can be promoted to understand an analysis result or can appropriately cope with the analysis result.

A vibration mechanism may be provided in the motion analysis display apparatus 20 or the sensor unit 10, and various pieces of information may be converted into vibration information by the vibration mechanism so as to be presented to the user 2.

The recorder 50 includes a communication section 52 which transmits image data captured by a video camera 51 to the motion analysis display apparatus 20 or receives a control command from the motion analysis display apparatus 20. The video camera 51 captures of images of swing actions of the user 2, and transmits captured image data to the communication section 52. The communication section 52 performs a process of transmitting the image data captured by the video camera 51 to the communication section 22 of the motion analysis display apparatus 20, or receiving a control command from the motion analysis display apparatus 20 and sending the control command to the video camera 51. The recorder 50 may not necessarily be provided in the swing analysis system 1. The recorder 50 is not limited to capturing moving image data, and may capture still image data.

According to the swing analysis system 1, analysis information obtained by analyzing a swing of the user (subject) 2 is presented on the display section 25 or the sound output section 26 of the motion analysis display apparatus 20 as a display apparatus on the basis of outputs from the inertial sensors (the acceleration sensor 12 and the angular velocity sensor 14) of the sensor unit 10 in response to an instruction from the processing section 21. The processing section 21 presents at least one index of swing analysis information generated by the swing analysis section 215 on the basis of the fact that the action detection section 213 determines that measurement of a swing of the golf club 3 as an exercise appliance is finished. Consequently, for example, since swing analysis information is automatically presented (for example, an image is displayed or a voice notification is performed) even without an instruction or the like from the user 2, the user 2 can obtain swing analysis information for each swing finishing timing even if the user 2 continuously performs swings with the golf club 3. Therefore, it is possible to improve convenience in that practice can be performed while continuously performing swings with the golf club 3. Therefore, the user 2 can perform practice with high efficiency.

The processing section 21 switches at least two presentation content items according to a set switching timing. Consequently, the user 2 can sequentially obtain at least two pieces of swing analysis information without giving an instruction. As mentioned above, it is possible to obtain a plurality of pieces of swing analysis information without troubling the user 2, and thus to further improve convenience.

In the swing analysis system 1, the operation section 23 as an input section which is used to input an index related to presented analysis information is provided in the motion analysis display apparatus 20 as a swing analysis apparatus. The user 2 selects an index to be presented from swing analysis information and inputs the index to the operation section 23 before starting a swing. As mentioned above, since analysis information desired to be presented after a swing is completed can be selected before the swing is started, it is possible to efficiently present swing analysis information desired to be obtained by the user 2, and thus to further improve convenience.

1-3. Operation Procedures of Swing Analysis (Motion Analysis) System

Figure 5:
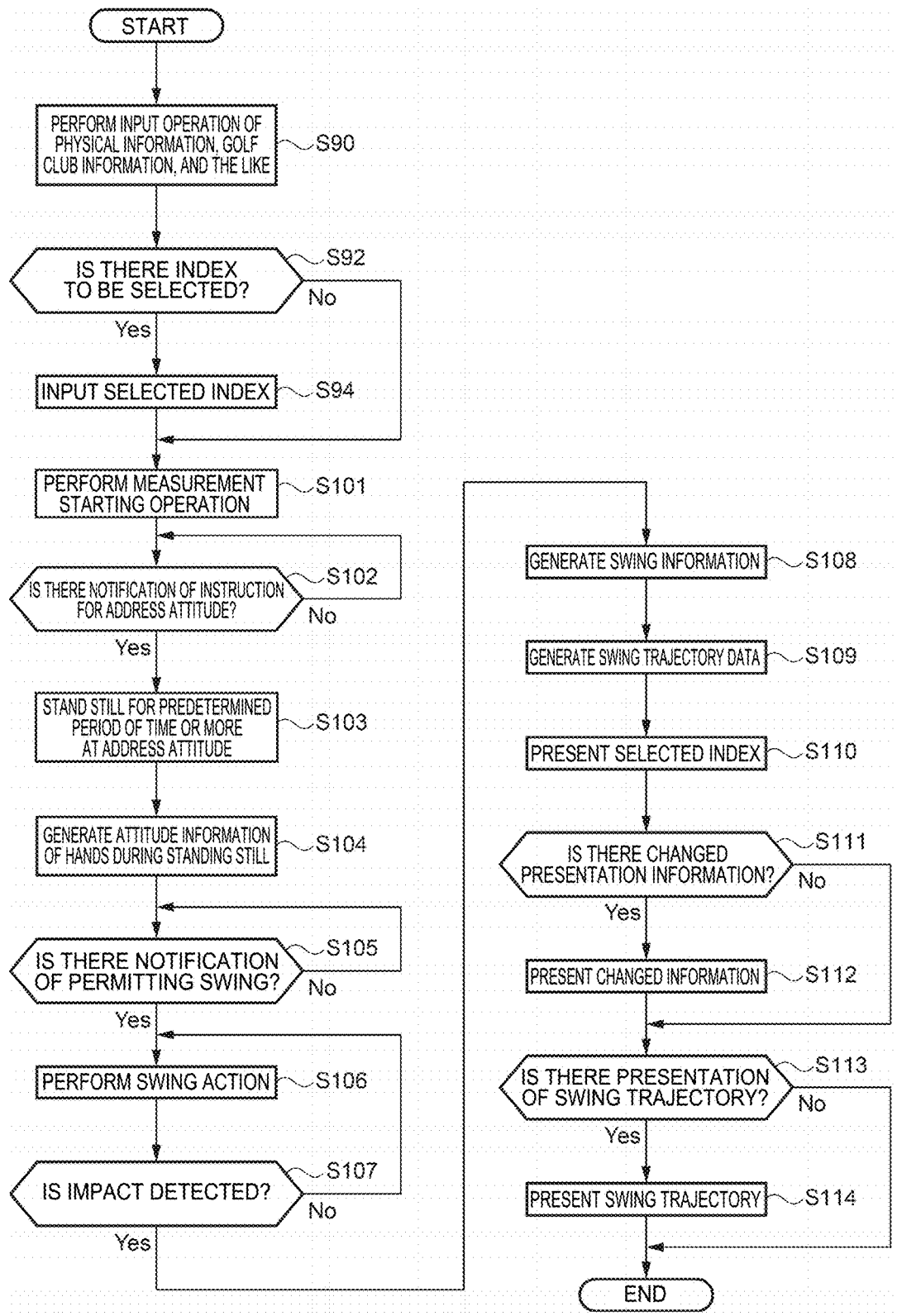
FIG. 5 is a flowchart illustrating operation procedures (an analysis result display method as an example of a presentation method) of the swing analysis system.
Figure 6:
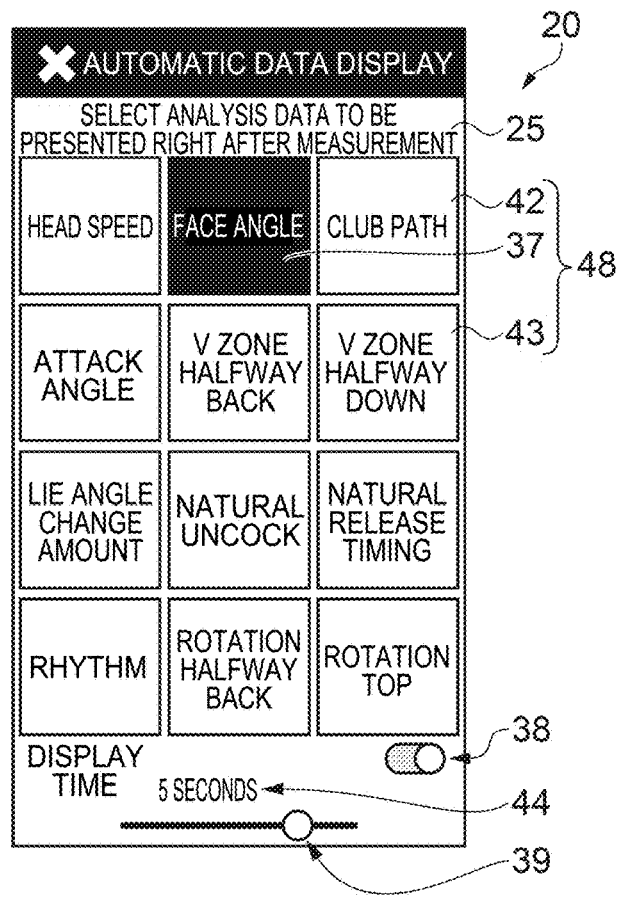
FIG. 6 is a diagram illustrating a display example of a setting screen for selecting and inputting an index of analysis information to be displayed.
Figure 7A:
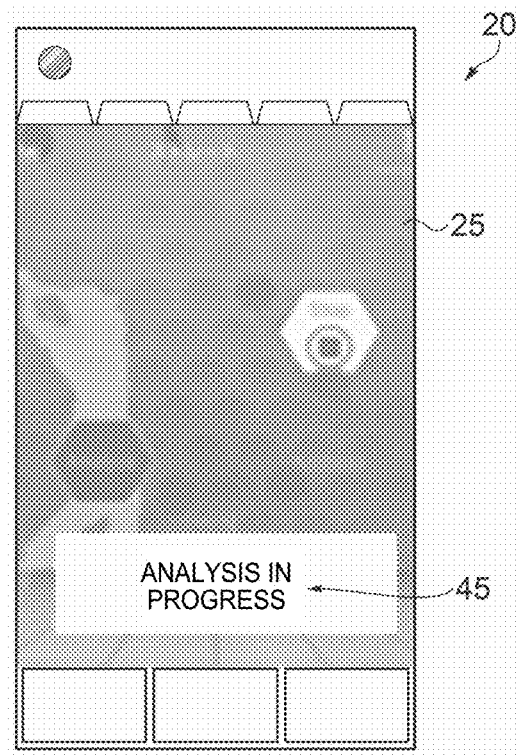
FIG. 7A is a diagram illustrating a display example of waiting for swing information to be displayed.
Figure 7B:
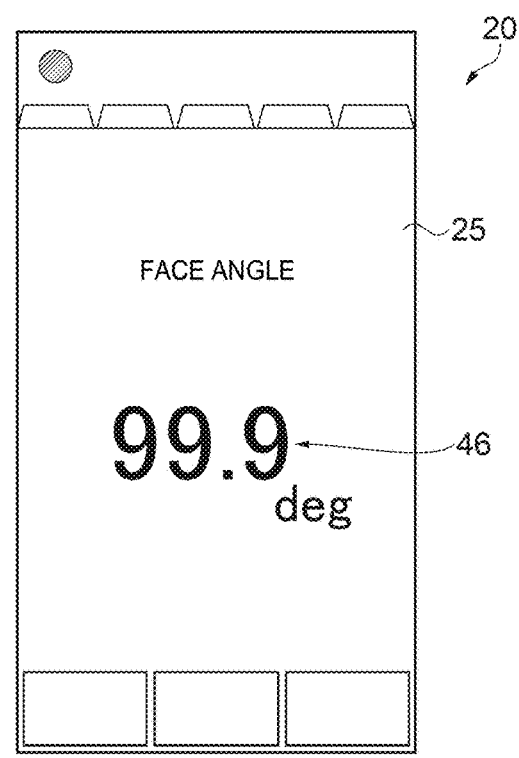
FIG. 7B is a diagram illustrating a display example of swing information.
Figure 8:
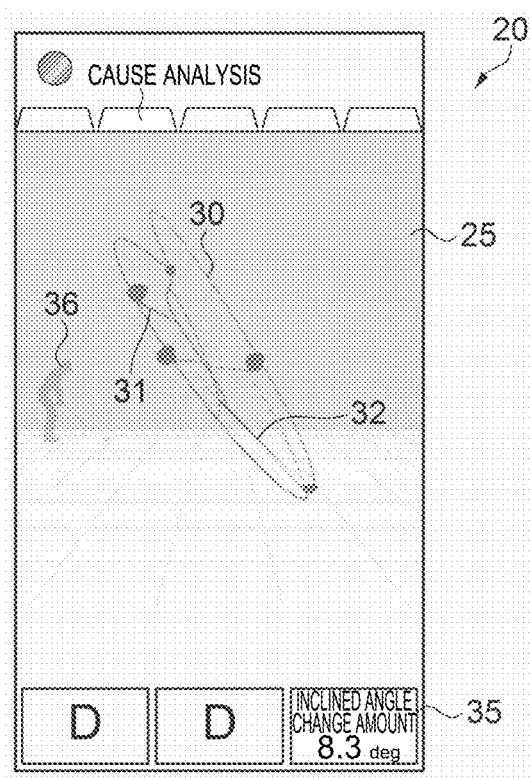
FIG. 8 is a diagram illustrating a display example including a swing trajectory.

Next, with reference to FIG. 5, a description will be made of operation procedures (an analysis result display method as an example of a presentation method) of the swing analysis (motion analysis) system 1, and swing actions of the user 2. In this example, presentation using image display will be described as presentation of analysis information as an example. The user (subject) 2 performs a series of swing actions for hitting the golf ball 4 as a target according to predefined procedures. FIG. 5 is a flowchart illustrating Example 1 indicating swing actions of the user 2, and swing analysis procedures performed by the swing analysis (motion analysis) system 1. With reference to FIGS. 6, 7A, 7B and 8, a description will be made of display (image display) as an example of presentation in the swing analysis (motion analysis) system 1. FIG. 6 is a diagram illustrating a display example of a setting screen. FIG. 7A is a diagram illustrating a display example of waiting for swing information to be displayed, and FIG. 7B is a diagram illustrating a display example of swing information. FIG. 8 is a diagram illustrating a display example including a swing trajectory. In the following description of the procedures, the reference numerals used for the constituent elements of the swing analysis (motion analysis) system 1 are used. The following operation procedures may be realized by the swing analysis system 1 causing a computer to execute the swing analysis program (motion analysis program) 240.

As illustrated in FIG. 5, first, the user 2 performs an input operation of the physical information 244 of the user 2, information (golf club information) regarding the golf club 3 used by the user 2, and the like via the motion analysis display apparatus 20 (step S90). The physical information 244 may include at least one of information regarding a height, a length of the arms, and a length of the legs of the user 2, and may further include information regarding sex or other information. The golf club information 242 includes at least one of information regarding a length (club length) of the golf club 3 and the type (number) of golf club 3.

In step S90, the user 2 inputs physical information such as a height, the sex, age, and country as the physical information 244, and inputs golf club information such as a club length, and a club number as the golf club information 242. Information included in the physical information 244 is not limited thereto, and, the physical information may include, for example, at least one of information regarding a length of the arms and a length of the legs instead of or along with the height. Similarly, information included in the golf club information 242 is not limited thereto, and, for example, the golf club information may not include at least one of information regarding the club length and the club number, and may include other information.

Next, the user 2 determines whether or not there is analysis information desired to be presented (displayed) in step S110 which will be described later (step S92). In a case where there is analysis information desired to be presented (displayed) (Yes in step S92), the user 2 selects the analysis information desired to be presented (displayed) in step S110 which will be described later, and inputs an index related to the analysis information to the operation section 23 as an input section (step S94). Consequently, the index related to analysis information desired to be presented (displayed) is set. FIG. 6 illustrates an example of a setting screen for selecting and inputting an index of analysis information to be presented (displayed). As illustrated in FIG. 6, assigned index buttons (for example, a face angle 37, a club path 42, and V zone halfway down 43) 48 are arranged in a matrix as a screen for providing an index to be selected on the display section 25. In other words, indexes which can be presented as analysis information are disposed to be listed in a single screen. The user 2 selects an index corresponding to selected analysis information from among the index buttons 48, and inputs the index by using the display section 25 as the operation section 23 (operation section). Specifically, in a case where a face angle is selected as an index, the user 2 may input the face angle by touching (pressing) a screen corresponding to a portion of the face angle 37 which is the index button 48 of the selected index among the index buttons 48. At this time, on the screen of the display section 25, the indicated (selected) index button 48 is highlighted, for example, by deepening a color as in the face angle 37 illustrated in FIG. 6. Through highlighting in the above-described way, it is possible to more easily recognize and perceive a selected index.

In step S92, display time (presentation time) of selected analysis information may be set. The display time (presentation time) of analysis information may be set by operating an adjustment button 39 provided on a lower part in the display section 25 illustrated in FIG. 6. In this case, as illustrated in FIG. 6, a set display time (presentation time) may be displayed as time display 44 (in this example, 5 seconds) which is numerical value information such as 3 seconds, 5 seconds, and 7 seconds. In step S92, whether or not analysis information will be changed in step S112 which will be described later may be set. In this case, it may be set whether or not analysis information will be changed and displayed by changing and operating a changing operation 38 provided on a lower part in the display section 25 illustrated in FIG. 6. In a case where analysis information will be changed and displayed, a plurality of indexes are input in the above step S94.

In a case where there is no analysis information desired to be presented (displayed) in step S92 (No in step S92), the flow proceeds to step S101.

Next, the user 2 performs a measurement starting operation (an operation for starting measurement in the sensor unit 10) via the motion analysis display apparatus 20 (step S101). If the user 2 performs the measurement starting operation in step S101, the sensor unit 10 (inertial sensor) measures three-axis accelerations and three-axis angular velocities in a predetermined cycle (for example, 1 ms), and sequentially transmits the measured data to the motion analysis display apparatus 20. Communication between the sensor unit 10 and the motion analysis display apparatus 20 may be wireless communication, and may be wired communication. This data indicates a position or an attitude of the sensor unit 10, and further indicates a position or an attitude of each portion of the golf club 3.

Next, after receiving a notification (for example, a notification using a voice) of giving an instruction for taking an address attitude (a basic attitude before starting a swing) from the motion analysis display apparatus 20 (Yes in step S102), the user 2 takes an address attitude so that the axis in the longitudinal direction of the shaft of the golf club 3 is perpendicular to a target line (target hit ball direction), and stands still for a predetermined period of time or more (step S103). Here, the motion analysis display apparatus 20 generates (acquires) attitude information of the hands 2a of the user 2 during standing still by using measured data output from the sensor unit 10 (step S104). In a case where the notification (for example, a notification using a voice) of giving an instruction for taking an address attitude (a basic attitude before starting a swing) from the motion analysis display apparatus 20 is not received (No in step S102), the user 2 waits for the notification to be received.

Next, the user 2 receives a notification (for example, a notification using a voice) of permitting a swing from the motion analysis display apparatus 20 (Yes in step S105), and then hits the golf ball 4 by performing a swing action (step S106). In a case where there is no notification (for example, a notification using a voice) of permitting a swing from the motion analysis display apparatus 20 (No in step S105), the user 2 delays a swing action until the notification of permitting a swing is received.

Next, the motion analysis display apparatus 20 determines whether or not impact (ball hitting) in the swing action of the user 2 in step S106 has been detected (step S107). In a case where it is determined that impact in the swing has been detected in step S107 (Yes in step S107), the motion analysis display apparatus 20 generates swing analysis information related to various indexes on the basis of measured data during the swing from the sensor unit 10 (step S108).

In a case where impact in the swing is not detected by the motion analysis display apparatus 20 (No in step S107), the user 2 returns to the swing action (step S106), and the user 2 performs a swing action again.

Next, the swing analysis section 215 of the motion analysis display apparatus 20 generates (acquires) swing trajectory information on the basis of obtained data of a series of swing actions (step S109).

Next, the motion analysis display apparatus 20 automatically displays, on the display section 25, swing analysis information corresponding to the index which is selected to be presented (displayed) and is input in step S94 among pieces of swing analysis information related to the various indexes generated in step S108 (step S110). Here, the "automatic presentation (display)" indicates that a process is performed in the motion analysis display apparatus 20 without receiving an instruction from the user 2, and performs presentation (display). In the above-described way, a presented analysis result is displayed as an image, and thus the user 2 can visually recognize the analysis result as image information. Consequently, it is possible to efficiently and objectively recognize or determine a swing state after the swing is completed without operating the motion analysis display apparatus 20.

Display examples will be described in detail with reference to FIGS. 7A and 7B. First, while the motion analysis display apparatus 20 is analyzing measured data, "analysis in progress" is displayed as illustrated in FIG. 7A. Swing analysis information related to various indexes generated on the basis of the fact that it is determined that impact in the swing has been detected (Yes in step S107) is automatically displayed as image information, for example, as illustrated in FIG. 7B. FIG. 7B illustrates an example of display of selected swing analysis information on the display section 25. In this example, analysis information of a face angle is displayed, and "99.9 deg" is displayed as numerical value information 46 of the face angle. This display may be changed to the original display (for example, the display illustrated in FIG. 7A) when the display time (presentation time) set in step S92 elapses.

As mentioned above, at least two display (presentation) content items are changed according to a set switching timing, and thus swing analysis information is obtained even without an instruction or the like from the user 2. In the above-described way, it is possible to efficiently obtain swing analysis information without troubling the user 2 and thus to further improve convenience.

The motion analysis display apparatus 20 may preferentially display analysis information corresponding to at least two indexes selected through an input operation performed by the user 2 among pieces of analysis information which are generated by using measured data obtained on the basis of a plurality of swings. Through the display, analysis information based on measurement of a plurality of swings is preferentially displayed, and thus the user 2 can easily understand a tendency of the plurality of swings which are repeatedly performed.

Next, the motion analysis display apparatus 20 determines whether or not there is presentation information displayed (presented) by changing an index (step S111). In a case where there is presentation information to be changed and displayed (presented) in step S111 (Yes in step S111), the motion analysis display apparatus 20 switches the display illustrated in FIG. 7B to display (not illustrated) of the next selected presentation information (analysis information) after the display time (presentation time) set in step S92 elapses (step S112). The changed display may be changed to the original display (for example, the display illustrated in FIG. 7A) after the display time (presentation time) set in step S92 elapses. In a case where there is no presentation information to be changed and displayed (presented) in step S111 (No in step S111), the flow proceeds to the next step S113 or proceeds to measurement of the next swing (step S106).

Switching from the display illustrated in FIG. 7B to display (not illustrated) of the next selected presentation information (analysis information) may be operated manually by the user.

As mentioned above, since at least two content items are changed according to a set switching timing, at least two pieces of swing analysis information can be sequentially obtained even without an instruction or the like from the user 2. In the above-described way, it is possible to obtain a plurality of pieces of swing analysis information without troubling the user 2, and thus to further improve convenience.

Next, the motion analysis display apparatus 20 determines whether or not a swing trajectory will be presented (displayed) (step S113). In a case where there is presentation information for displaying (presenting) a swing trajectory in step S113 (Yes in step S113), the motion analysis display apparatus 20 displays (presents), for example, a swing trajectory 30 approximating a swing action as illustrated in FIG. 8 after displaying (presenting) the selected analysis information (step S114).

In the display example illustrated in FIG. 8, the swing trajectory is displayed on the display section 25 of the motion analysis display apparatus 20. A series of swing actions of the user 2 is displayed as the swing trajectory 30 on the display section 25. In display of the swing trajectory 30, a trajectory of a series of swing trajectories 30 is displayed by displaying a state of the golf club 3 at each time point (timing), for example, a golf club image 31 during a backswing, with a golf club image 32 as a swing starting timing. The golf club image 32 may be an image at impact.

In this example, the swing trajectory 30 is displayed as an image viewed from the rear side, that is, an image viewed from an opposite side to the golf ball 4 side among front views viewed from directions intersecting the hitting surface of the golf ball 4 (refer to FIG. 1) of the head 3a (refer to FIG. 1) of the golf club 3 (refer to FIG. 1). As a mark indicating this viewing direction, a mark 36 is displayed. Regarding a display direction, an image viewed from the golf ball 4 side may be displayed. A display window 35 showing other analysis information may be displayed on a part of the display section 25 (a lower right part in the screen in this example).

The swing trajectory 30 may be displayed in an overlapping manner with the display (presentation) of the analysis information in step S110 or in step S112. In this case, this step S113 is performed before step S110.

Regarding display (presentation) in the above steps S110, S112 and S113, for example, comment such as advice information is preferably displayed (presented) along with display (presentation) of analysis information. As mentioned above, if comment is presented along with an index of analysis information, the user 2 can be promoted to understand an analysis result or can appropriately cope with the analysis result. Since advice information is presented, it is possible to accurately cope with improvement of a swing.

Through the above-described steps, a series of operation procedures of the swing analysis (motion analysis) system 1 and the user 2 in this embodiment are finished.

According to the above-described operation procedures (analysis result display method as a presentation method) of swing actions, it is possible to determine finishing of measurement of a swing of an exercise appliance (golf club 3) using an inertial sensor (sensor unit 10) and to present at least one index of analysis information regarding the measured swing on the basis of determination of finishing. As mentioned above, since swing analysis information is presented for each swing finishing timing even without an instruction or the like from the user, the user 2 can obtain swing analysis information for each swing finishing timing even if the user 2 continuously performs swings with the exercise appliance. Therefore, it is possible to improve convenience and to perform highly efficient practice in that the user 2 can perform practice while continuously performing swings with an exercise appliance.

Prior to step S101 in which the user 2 performs a measurement starting operation (an operation for starting measurement in the sensor unit 10) via the motion analysis display apparatus 20, there is provided step S94 in which the user 2 selects and inputs an index related to some of analysis information to be presented (displayed) in step S110. Consequently, since the user 2 can select an index to be presented before measurement of a swing is started among pieces of swing analysis information, it is possible to efficiently present swing analysis information desired to be understood by the user 2, and thus to further improve convenience.

In the display (presentation) of analysis information in step S110 or step S112, information associated with analysis information corresponding to a displayed (presented) index among pieces of analysis information regarding a swing which is different from the present swing may also be displayed (presented). According to this display (presentation), since a presented index of analysis information regarding a swing is displayed along with an index of analysis information regarding a different swing, corresponding to some (index) of the analysis information regarding the swing, the user 2 can compare the pieces of analysis information regarding the different swings with each other, so as to objectively determine a difference between the swings or to easily determine the quality of a swing state.

In step S94, target values of various analysis data items may be input to the operation section 23 so as to be set in advance as information to be presented (displayed) in step S110 which will be described later, and comparison information between analysis data and the set target values may be presented when presentation (display) in step S110 is performed. For example, there may be a configuration in which a target range is set in advance, and information such as "OK" or "NG" is presented depending on analysis data is included in the set range. Through this presentation, the user 2 can easily and accurately determine the quality of a swing state.

In the above description, presentation of analysis information using image display has been described as an example, but presentation of analysis information may be performed by using voice information. In the above-described way, if a notification of analysis information is performed by using voice information, the user 2 can obtain an analysis result while performing a swing, and can thus perform more efficient practice.

Figure 9:
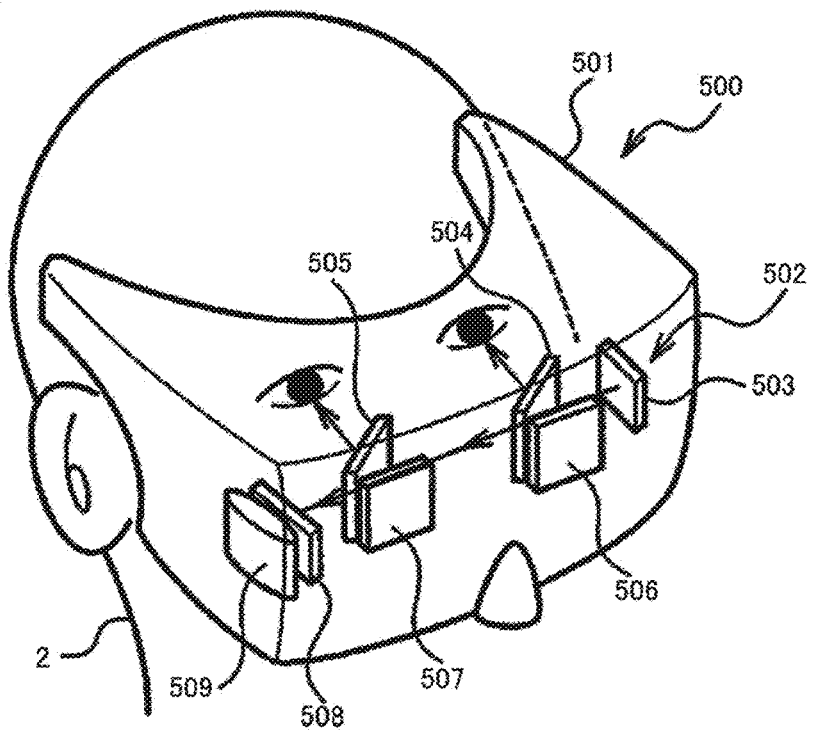
FIG. 9 is a perspective view illustrating a head mounted display as an example of a motion analysis display apparatus.

Next, with reference to FIG. 9, a description will be made of an example of using a head mounted display (HMD) as the motion analysis display apparatus 20. FIG. 9 is a perspective view illustrating a head mounted display (HMD) as a motion analysis display apparatus.

1-4. Application 1 of Motion Analysis Display Apparatus

As illustrated in FIG. 9, a head mounted display (HMD) 500 includes a spectacle main body 501 mounted on the head of the user 2. The spectacle main body 501 is provided with a display section 502. The display section 502 integrates a light beam emitted from an image display unit 503 with a light beam directed toward the eyes of the user 2 from the external world, and thus overlaps a virtual image on the image display unit 503 with a real image of the external world viewed from the user 2.

The display section 502 is provided with, for example, the image display unit 503 such as an liquid crystal display (LCD), a first beam splitter 504, a second beam splitter 505, a first concave reflection mirror 506, a second concave reflection mirror 507, a shutter 508, and a convex lens 509.

The first beam splitter 504 is disposed on the front side of the left eye of the user 2, and partially transmits and partially reflects light emitted from the image display unit 503. The second beam splitter 505 is disposed on the front side of the right eye of the user 2, and partially transmits and partially reflects light which is partially transmitted from the first beam splitter 504.

The first concave reflection mirror 506, which is disposed in front of the first beam splitter 504, partially reflects the partially reflected light from the first beam splitter 504 so as to transmit the light through the first beam splitter 504, and thus guides the light to the left eye of the user 2. The second concave reflection mirror 507, which is disposed in front of the second beam splitter 505, partially reflects the partially reflected light from the second beam splitter 505 so as to transmit the light through the second beam splitter 505, and thus guides the light to the right eye of the user 2.

The convex lens 509 guides partially transmitted light from the second beam splitter 505 to the outside of the head mounted display (HMD) 500 when the shutter 508 is opened.

The analysis information (refer to FIG. 7B) in a series of swing actions of the user 2, the swing information such as the swing trajectory 30 (refer to FIG. 8) approximating the swing actions, and the like, as described in the display examples, are displayed on the head mounted display (HMD) 500. The display (presentation) content is the same as in the above-described display examples, and a detailed description thereof will be omitted.

According to the head mounted display (HMD) 500, since the head mounted display (HMD) is mounted on the head and displays information, the user 2 can understand swing information of the user or attitude (position) information of the hands 2a without holding the motion analysis display apparatus 20 including the display section 25 displaying information with the hands.

The head mounted display (HMD) 500 may have the functions of the motion analysis display apparatus 20 and may display swing analysis or swing information based measured data from the sensor unit 10, and may be used as a display section displaying image data transmitted from the separate motion analysis display apparatus 20. The functions of the motion analysis display apparatus (display apparatus) 20 include the processing section 21 (an example of a processing section), the communication section 22, the operation section 23, the storage section 24, the display section 25, the sound output section 26, and the imaging section 27 as described above.

Figure 10:
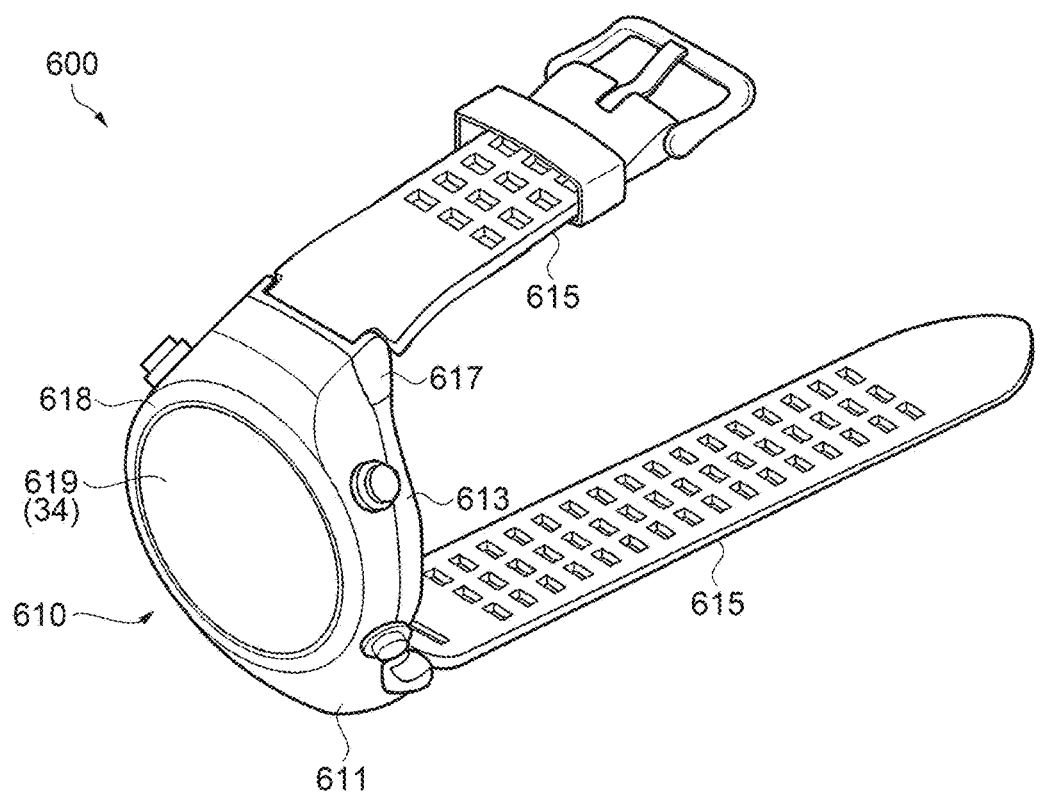
FIG. 10 is a perspective view illustrating an arm mounted motion analysis display apparatus as an example of a wearable apparatus.

Next, with reference to FIG. 10, a description will be made of an example of using an arm mounted analysis display apparatus as an example of a wearable apparatus, as the motion analysis display apparatus. FIG. 10 is a perspective view illustrating an arm mounted motion analysis display apparatus as an example of a wearable apparatus.

1-5. Application 2 of Motion Analysis Display Apparatus

As illustrated in FIG. 10, a wearable (arm mounted) analysis display apparatus 600 is mounted on a predetermined part (the wrist in this example) of the user (subject) 2 (refer to FIG. 1) and displays swing analysis or swing information based on measured data from the sensor unit 10 (refer to FIG. 1). The analysis display apparatus 600 includes an apparatus main body 610 which is worn by the user 2 and displays swing analysis information such as swing analysis or attitude information of the hands 2a (refer to FIG. 1) of the user 2, and a band portion 615 which is attached to the apparatus main body 610 and allows the apparatus main body 610 to be mounted on the user 2.

The apparatus main body 610 of the analysis display apparatus 600 is provided with a bottom case 613 on the side mounted on the user 2, and a top case 611 on an opposite side to the side mounted on the user 2. A bezel 618 is provided on a top side (top case 611) of the apparatus main body 610, and a glass plate 619 as a top plate portion (outer wall) which is disposed inside the bezel 618 and protects inner structures is also provided. A pair of band attachment portions 617 which is a connection portion with the band portion 615 are provided on both sides (Y axis direction) of the bottom case 613.

The apparatus main body 610 is provided with a display section such as a liquid crystal display (LCD 634) directly under the glass plate 619. The user 2 can view swing analysis information, attitude information of the hands 2a of the user 2, or the like, displayed on the liquid crystal display (LCD 634) via the glass plate 619. The apparatus main body 610 may include the processing section 21, the communication section 22, the operation section 23, the storage section 24, the display section 25, the sound output section 26, and the imaging section 27, in the same manner as the motion analysis display apparatus 20 described with reference to FIG. 4. The display section 25 corresponds to a display section such as the liquid crystal display (LCD 634) in this example.

The analysis information (refer to FIG. 7B) in a series of swing actions of the user 2, the swing information such as the swing trajectory 30 (refer to FIG. 8) approximating the swing actions, and the like, as described in the display examples, are displayed on the display section of the liquid crystal display (LCD 634). The display (presentation) content is the same as in the above-described display examples, and a detailed description thereof will be omitted.

Other advice information based on swing analysis results, for example, a text image representing a swing type of the user 2 or a text image representing advice (practice method or the like) suitable for the swing type of the user 2 may be displayed on the display section of the liquid crystal display (LCD 634). Moving images as video pictures may be displayed on the display section of the liquid crystal display (LCD 634).

In the above description, an example in which the top plate portion of the apparatus main body 610 is implemented by the glass plate 619 has been described, but the top plate portion may be formed by using materials other than glass, such as transparent plastic, as long as a member is transparent so as to allow the LCD 634 to be viewed, and has the rigidity of being capable of protecting constituent elements included in the top case 611 and the bottom case 613, such as the LCD 634. A configuration example in which the bezel 618 is provided has been described, but the bezel 618 may not be provided.

According to the wearable (arm mounted) analysis display apparatus 600, since the analysis display apparatus is mounted on the arm and displays information, the user 2 can understand swing information of the user or attitude (position) information of the hands 2a without holding the display section (liquid crystal display (LCD 634)) displaying information with the hands.

The wearable (arm mounted) analysis display apparatus 600 may have the functions of the motion analysis display apparatus 20 and may display swing analysis or swing information based measured data from the sensor unit 10, and may be used as a display section displaying image data transmitted from the separate motion analysis display apparatus 20. The functions of the motion analysis display apparatus (display apparatus) 20 include the processing section 21 (an example of a processing section), the communication section 22, the operation section 23, the storage section 24, the display section 25, the sound output section 26, and the imaging section 27 as described in the motion analysis display apparatus 20 of the above-described embodiment.

For example, the invention includes substantially the same configuration (for example, a configuration in which functions, methods, and results are the same, or a configuration in which objects and effects are the same) as the configuration described in the embodiment. The invention includes a configuration in which an inessential part of the configuration described in the embodiment is replaced with another part. The invention includes a configuration which achieves the same operation and effect or a configuration capable of achieving the same object as in the configuration described in the embodiment. The invention includes a configuration in which a well-known technique is added to the configuration described in the embodiment.

The entire disclosure of Japanese Patent Application No. 2016-005848 filed Jan. 15, 2016 is expressly incorporated by reference herein.

What is claimed is:

1. A presentation method comprising:
in response to detecting completion of a swing of an exercise appliance by a user:
performing an analysis on the swing by using output data from an inertial sensor measuring the swing of the exercise appliance;
automatically displaying, without a user input, analysis information based on a first preset index among a plurality of preset indices regarding the swing; and after displaying the analysis information based on the first preset index for a predetermined time, automatically switching, without a user input, the analysis information that is displayed from the analysis information based on the first preset index to analysis information based on a second preset index different from the first preset index among the plurality of preset indices, wherein
the predetermined time is dynamically adjustable by the user performing the swing.

2. The presentation method according to claim 1, wherein:
the analysis information that is displayed is automatically switched to present analysis information based on each one of the plurality of preset indices in a sequential order; and
the automatic switching occurs at a preset switching timing.

3. The presentation method according to claim 1, comprising:
setting the plurality of preset indices before performing the analysis.

4. The presentation method according to claim 1, wherein:
the analysis information that is displayed is automatically switched to preferentially present analysis information based on each one of the plurality of preset indices according to a plurality of pieces of swing analysis information.

5. The presentation method according to claim 1, wherein:
the analysis information based on the first preset index is displayed along with analysis information based on the first preset index regarding another swing which is different from the analyzed swing.

6. The presentation method according to claim 1, wherein:
the analysis information based on the first preset index is displayed as image information.

7. The presentation method according to claim 1, comprising:
presenting analysis information based on one preset index among the plurality of preset indices as voice information.

8. The presentation method according to claim 1, wherein:
display a comment along with the analysis information based on the first preset index.

9. The presentation method according to claim 8, wherein the comment is advice information.

10. The presentation method according to claim 1, wherein:
a swing trajectory is displayed along with the analysis information based on the first preset index.

11. A swing analysis apparatus comprising:
a processor programmed to:
in response to detecting completion of a swing of an exercise appliance by a user:
perform an analysis on the swing by using output data from an inertial sensor measuring the swing of the exercise appliance, so as to generate analysis information based on a plurality preset indices;
automatically display, without a user input, analysis information based on a first preset index among the plurality of preset indices; and
after displaying the analysis information based on the first preset index for a predetermined time, automatically switch, without a user input, the analysis information that is displayed from the analysis information based on the first preset index to analysis information based on a second preset index different from the first preset index among the plurality of preset indices, wherein
the predetermined time is dynamically adjustable by the user performing the swing.

12. The swing analysis apparatus according to claim 11, wherein the processor is programmed to:
the automatic switching occurs at a preset switching timing.

13. The swing analysis apparatus according to claim 11, wherein the processor is programmed to:
receive an input to set the plurality of preset indices before the swing is analyzed.

14. The swing analysis apparatus according to claim 11, wherein the processor is programmed to:
automatically switch the analysis information that is displayed to preferentially present analysis information based on each one of the plurality of preset indices according to a plurality of pieces of swing analysis information.

15. The swing analysis apparatus according to claim 11, wherein the processor is programmed to:
display the analysis information based on the first preset index along with analysis information based on the first preset index regarding another swing which is different from the analyzed swing.

16. The swing analysis apparatus according to claim 11, wherein the processor is programmed to:
display the analysis information based on the first preset index as image information.

17. The swing analysis apparatus according to claim 11, wherein the processor is programmed to:
present analysis information based on one preset index among the plurality of as voice information.

18. The swing analysis apparatus according to claim 11, wherein the processor is programmed to:
display a comment along with the analysis information based on the first preset index.

19. The swing analysis apparatus according to claim 18, wherein the comment is advice information.

20. The swing analysis apparatus according to claim 11, wherein the processor is programmed to:
display a swing trajectory along with the analysis information based on the first preset index.

21. A swing analysis system comprising:
the swing analysis apparatus according to claim 11; and
the inertial sensor.

22. A non-transitory recording medium storing a program causing a computer to execute:
in response to detecting completion of a swing of an exercise appliance by a user:
performing an analysis on the swing by using output data from an inertial sensor measuring the swing of the exercise appliance;
automatically displaying, without a user input, analysis information based on a first preset index among a plurality of preset indices regarding the swing; and
after displaying the analysis information based on the first preset index for a predetermined time, automatically switching, without a user input, the analysis information that is displayed from the analysis information based on the first preset index to analysis information based on a second preset index different from the first preset index among the plurality of preset indices, wherein the predetermined time is dynamically adjustable by the user performing the swing.

* * * * *